(12) United States Patent
Zuo et al.

(10) Patent No.: US 12,070,465 B2
(45) Date of Patent: Aug. 27, 2024

(54) COMPOSITIONS AND METHODS FOR THE PREVENTION AND TREATMENT OF HEARING LOSS

(71) Applicant: Ting Therapeutics LLC, Omaha, NE (US)

(72) Inventors: Jian Zuo, Omaha, NE (US); Jeff North, Omaha, NE (US); Santanu Hati, Omaha, NE (US); Marisa Laura Zallocchi, Omaha, NE (US)

(73) Assignee: Ting Therapeutics LLC, Omaha, NE (US)

( * ) Notice: Subject to any disclaimer, the term of this patent is extended or adjusted under 35 U.S.C. 154(b) by 0 days.

(21) Appl. No.: 18/031,998

(22) PCT Filed: Sep. 15, 2021

(86) PCT No.: PCT/US2021/050425
§ 371 (c)(1),
(2) Date: Apr. 14, 2023

(87) PCT Pub. No.: WO2022/060811
PCT Pub. Date: Mar. 24, 2022

(65) Prior Publication Data
US 2023/0330097 A1    Oct. 19, 2023

Related U.S. Application Data

(60) Provisional application No. 63/078,571, filed on Sep. 15, 2020.

(51) Int. Cl.
*A61K 31/55* (2006.01)
*A61K 31/397* (2006.01)
(Continued)

(52) U.S. Cl.
CPC ............ *A61K 31/55* (2013.01); *A61K 31/397* (2013.01); *A61K 31/45* (2013.01); *A61P 27/16* (2018.01)

(58) Field of Classification Search
CPC .............. A61K 2300/00; A61K 31/397; A61K 31/4015; A61K 31/4025; A61K 31/4412;
(Continued)

(56) References Cited

FOREIGN PATENT DOCUMENTS

KR        20150122470 A      11/2015

OTHER PUBLICATIONS

Du et al.(Pharmazie 67, (2012), pp. 559-563) (Year: 2012).*
(Continued)

*Primary Examiner* — Savitha M Rao
(74) *Attorney, Agent, or Firm* — Veritas Group IP, PLLC; Susan B. Fentress

(57) ABSTRACT

In one aspect, use of compounds as active agents to treat a hearing impairment and to prevent a hearing impairment, and methods of treating and/or preventing hearing impairments or disorders using the compositions are disclosed. (E)-1-(3-(3,4,5-trimethoxyphenyl)acryloyl)-5,6-dihydropyridin-2(1H)-one and derivatives exhibit excellent protection against antibiotic-induced hearing loss in zebrafish and mice. In one aspect, (E)-1-(3-(3,4,5-trimethoxy phenyl)acryloyl)-5,6-dihydropyridin-2(1H)-one and derivatives can be used as a therapy for the treatment and/or prevention of hearing loss. This abstract is intended as a scanning tool for purposes of searching in the particular art and is not intended to be limiting of the present invention.

12 Claims, 11 Drawing Sheets

(51) Int. Cl.
*A61K 31/45* (2006.01)
*A61P 27/16* (2006.01)
(58) Field of Classification Search
CPC .... A61K 31/45; A61K 31/4525; A61K 31/55; A61K 33/243; A61K 45/06; A61P 27/16; C07D 205/08; C07D 207/267; C07D 211/76; C07D 223/10; C07D 405/06; C07D 409/06
See application file for complete search history.

(56) References Cited

OTHER PUBLICATIONS

Du, Fei Xiao, Ethanol Extract of Piper Longum L. attenuated gentamicin induced hair cell loss in neonatal cochlea cultures, Pharmazie 67:559-563 (2012).
Hoshino, Tomofumi, Protective Role of Nrf2 in Age-Related Hearing Loss and Gentamicin Ototoxicity, manuscript.
International Search Report PCT/US2021/050425 dated Aug. 2, 2022.
IPER PCT/US2021/050425 dated May 10, 2022.

* cited by examiner

Reduction conditions for reduced

Synthesis of β-aryl-α,β-unsaturated sulfonamides

COMPOSITIONS AND METHODS FOR THE PREVENTION AND TREATMENT OF HEARING LOSS

Cross-reference to related applications: This application claims the benefit of U.S. provisional patent application Ser. No. 63/078,571 filed Sep. 15, 2020, under 35 USC § 119(e) and 35 U.S.C. § 111(a) (hereby specifically incorporated herein by reference).

Statement regarding federally sponsored research or development: This invention was made with government support under R01DC015010 R01DC015444 R43DC019065 from the NIH, N00014-18-1-2507 from the Navy/ONR, and W81XWH-18-1-0442 from the Army/MRMC. The government has certain rights in the invention.

BACKGROUND OF THE INVENTION

(1) Field of the Invention

The present invention relates to therapeutic uses of active agents such as for treating, inhibiting, and/or preventing hearing loss.

(2) Description of Related Art Including Information Disclosed Under 37 CFR 1.97 and 37 CFR 1.98

Over 35 million Americans suffer from hearing impairment. In mammals, hair cell impairment is permanent. Antibiotic-induced hearing impairment (AIHL) is a permanent side effect from often necessary medical care. Neonates admitted to the neonatal intensive care unit have ten times the rate of hearing loss as neonates not admitted, often associated with the administration of antibiotics. The spiral-shaped cochlea of the inner ear is responsible for detecting sound. Inner hair cells lining the cochlea transform the mechanical vibrations of sound waves into chemical signals. These chemicals are then released from the hair cells and received by receptors on the auditory nerve fibers that send electrical impulses to the brain. The inner ear cells lining the cochlea can be destroyed by the use of antibiotics, leading to a condition called sensorineural hearing impairment.

Currently, there are no clinically proven medications for the treatment of hearing impairment (sensorineural and neural), or tinnitus associated with the inner ear, and a medication that could be used to prevent, alleviate, or eliminate hearing impairment (or tinnitus) would thus be very desirable. The most common remedy for individuals suffering from severe sensorineural hearing impairment is a hearing aid, which functions to amplify sound. Hearing aids are non-invasive and can improve an individual's ability to hear. However, hearing aids can often be quite conspicuous and embarrassing to the wearer and hearing aids do not return hearing to normal levels. Furthermore, hearing aids amplify sound indiscriminately, sometimes amplifying sounds that an individual does not wish to hear, such as environmental noise. There exists a need in the art for a solution to hearing impairment due to antibiotics.

BRIEF SUMMARY OF THE INVENTION

The invention provides a method to prevent or treat hearing loss including the steps of administering to an animal or human in need thereof an effective amount of a pharmaceutical composition containing a therapeutically active agent, wherein the therapeutically active agent includes: Piperlongumine (E)-1-(3-(3,4,5-trimethoxyphenyl)acryloyl)-S,6-dihydropyridin-2(1H)-one and derivatives thereof.

The inventive subject matter also includes a composition for use in preventing or treating hearing loss by protecting inner ear cells from death wherein the composition is an effective amount of an active agent, wherein the active agent includes: Piperlongumine (E)-1-(3-(3,4,5-trimethoxyphenyl)acryloyl)-S,6-dihydropyridin-2(1H)-one and derivatives thereof.

The inventive subject matter also includes a kit made of an active agent, wherein the active agent includes: Piperlongumine (E)-1-(3-(3,4,5-trimethoxyphenyl)acryloyl)-S,6-dihydropyridin-2(1H)-one and derivatives thereof or a pharmaceutically acceptable salt thereof; and one or more of: (A) at least one antibiotic; (B) at least one cancer drug; or (C) instructions for preventing a hearing impairment.

BRIEF DESCRIPTION OF THE SEVERAL VIEWS OF THE DRAWING

The accompanying figures, which are incorporated in and constitute a part of this specification, illustrate several aspects and together with the description serve to explain the principles of the invention.

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
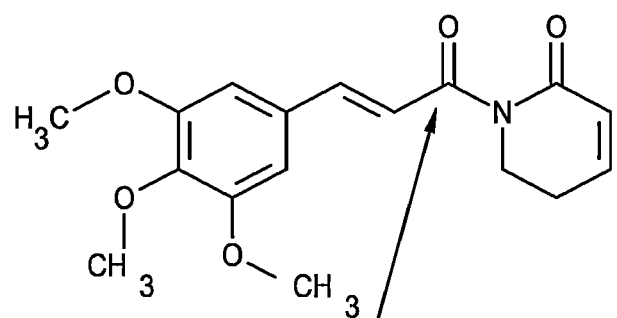
FIG. 1A is an illustration showing (E)-1-(3-(3,4,5-trimethoxyphenyl)acryloyl)-S,6-dihydropyridin-2(1H)-one (Piperlongumine) having a structure represented by the formula as shown.

The present invention can be understood more readily by reference to the following detailed description of the invention and the examples included therein. Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

In one aspect, compounds can be used as a therapy for the treatment and/or prevention of hearing loss. In various aspects, the compounds and compositions of the invention can be administered in pharmaceutical compositions, which are formulated according to the intended method of administration. The compounds of this invention are defined as a therapeutically active agent in a treatment regimen or procedure that is intended for preventing hearing loss by noise or aging by protecting inner ear cells from death and in preventing hearing loss by chemotherapy or antibiotics induced hearing loss. Therapeutic agent means a chemical substance that is used for the treatment or mitigation of a disease condition or ailment.

In one aspect, compounds can be used as a therapy for the treatment and/or prevention of hearing loss. In various aspects, the compounds and compositions of the invention can be administered in pharmaceutical compositions, which are formulated according to the intended method of administration. The compounds of this invention are defined as a therapeutically active agent in a treatment regimen or procedure that is intended for preventing hearing loss by noise or aging by protecting inner ear cells from death and in preventing hearing loss by chemotherapy or antibiotics induced hearing loss. Therapeutic agent means a chemical substance that is used for the treatment or mitigation of a disease condition or ailment.

Now referring to FIG. 1, Piperlongumine. (E)-1-(3-(3,4,5-trimethoxyphenyl)acryloyl)-S,6-dihydropyridin-2(1H)-one, is shown. Piperlongumine is an alkaloid, which is extracted from *Piper longum* Linn. It exhibits anti-atherosclerotic, anxiolytic, antidiabetic, antidepressant, antibacterial, anti-platelet, aggregation, anxiolytic and anti-inflammatory properties. Piperlongumine prevents the production of tumor necrosis factor-α and interleukin-6. It is also referred to as Piplartin, 5,6-Dihydro-1-[(2E)-1-oxo-3-(3,4,5-trimethoxyphenyl)-2-propen-1-yl]-2(1H)-Pyridinone, Piplartine, 5,6-Dihydro-1-(1-oxo-3-[3,4,5-trimethoxyphenyl]-trans-2-propenyl)-2[1H]-pyridinone.

A number of derivatives of Piperlongumine similarly show efficacy as a therapy for the treatment and/or prevention of hearing loss. The generic structures of derivatives within the scope of this invention are shown. More specifically, acryloyl derivatives are contemplated. The acryloyl group is a form of enone with structure $H_2C=CH-C(=O)-$; it is the acyl group derived from acrylic acid.

Derivatives of Piperlongumine are formed from the structure:

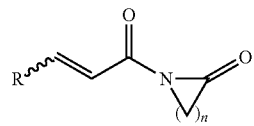

Wavy bond indicated E and Z isomers.

N=1, 2, 3, 4, 5, 6

R=H, alkyl, hydroxy, thiol, halogen, acid, ester, amide, amine, substituted alkyl chain, substitutedcyclic alkyl ring, heterocycle, piperidine, cyclohexanol, heteroaromatic, substituted heteroaromatic, cyclo alipthatic, hetero-cyclo aliphatic ring. In another aspect, derivatives of Piperlongumine are formed from the structure:

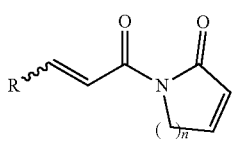

Wavy bond indicated E and Z isomers.

N=0, 1, 2, 3, 4

R=H, alkyl, alkoxy, hydroxy, thiol, halogen, acid, ester, amide, amine, substituted alkyl chain, substituted cyclic alkyl ring, heterocycle, piperidine, cyclohexano,l heteroaromatic, substituted heteroaromatic, cycloalipthatic, heterocyclo aliphatic ring. The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl. A cyclic compound (or ring compound) is a term for a compound in the field of chemistry in which one or more series of atoms in the compound is connected to form a ring. Rings may vary in size from three to many atoms, and include examples where all the atoms are carbon (i.e., are carbocycles), none of the atoms are carbon (inorganic cyclic compounds), or where both carbon and non-carbon atoms are present (heterocyclic compounds).

Figure 1B:
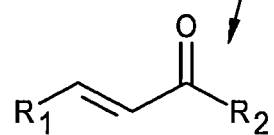
FIG. 1B is an illustration showing the formula of derivatives of Piperlongumine.

The base structure of derivatives of Piperiongumine is shown in FIG. 1B and Table 1 is:

$R_1$=2-furanyl, 2-thiophenyl, phenyl 3-methoxyphenyl, 3-trifluromethylphenyl, 4-trifuloromethylphenyl, 4-chloro, 4-nitro, 2,2-difluoro-1,3-benzodioxole, 2-naphthyl; and $R_2$=N-linked Bets-, Gamma-, Delta-, or Epsilon-lactam.

Table 1

TABLE 1

| Compound ID | Structure | m/z | Mol For | IW | FW | NET Wt (mg) |
|---|---|---|---|---|---|---|
| SHJ-1 | 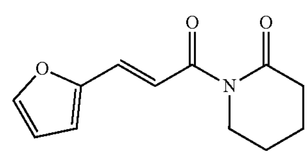 [SMILES: O=C(/C=C/c1ccco1)N1CCCCC1=O] | 219.0895 | $C_{12}H_{13}NO_3$ | 948.4 | 968.5 | 20.1 |
| SHJ-2 | 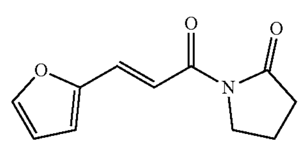 [SMILES: O=C(/C=C/c1ccco1)N1CCCC1=O] | 205.0739 | $C_{11}H_{11}NO_3$ | 974 | 984.1 | 10.1 |
| SHJ-3 | 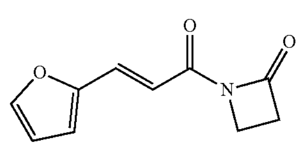 [SMILES: O=C(/C=C/c1ccco1)N1CCC1=O] | 191.0582 | $C_{10}H_9NO_3$ | 1005 | 1013.4 | 8.4 |
| SHJ-4 | 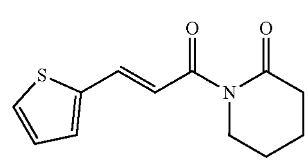 [SMILES: O=C(/C=C/c1cccs1)N1CCCCC1=O] | 235.0667 | $C_{12}H_{13}NO_2S$ | 971.7 | 977.6 | 5.9 |
| SHJ-5 | 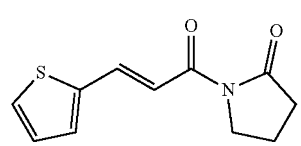 [SMILES: O=C(/C=C/c1cccs1)N1CCCC1=O] | 221.051 | $C_{11}H_{11}NO_2S$ | 966.2 | 973.1 | 6.9 |

TABLE 1-continued
| Compound ID | Structure | m/z | Mol For | IW | FW | NET Wt (mg) |
|---|---|---|---|---|---|---|
| SHJ-6 | 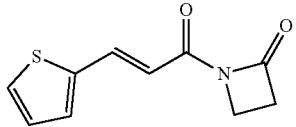 | 207.0354 | $C_{10}H_9NO_2S$ | 978 | 982.1 | 4.1 |
| SHJ-16 | 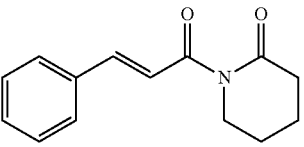 [SMILES: O=C(/C=C/c1ccccc1)N1CCCCC1=O] | 229.1103 | $C_{14}H_{15}NO_2$ | 942.4 | 950 | 7.6 |
| SHJ-17 | 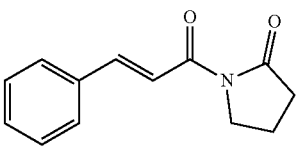 [SMILES: O=C(/C=C/c1ccccc1)N1CCCC1=O] | 215.0946 | $C_{13}H_{13}NO_2$ | 948.1 | 957.7 | 9.6 |
| SHJ-18 | 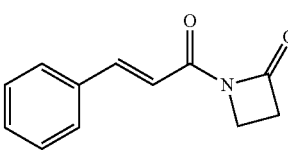 | 201.079 | $C_{12}H_{11}NO_2$ | 947.8 | 953 | 5.2 |
| SHJ-25 | 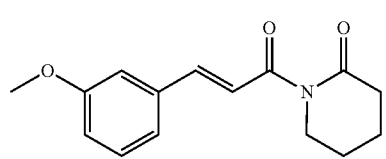 [SMILES: COc1cccc(/C=C/C(=O)N2CCCCC2=O)c1] | 259.1208 | $C_{15}H_{17}NO_3$ | 988.3 | 997.3 | 9 |
| SHJ-26 | 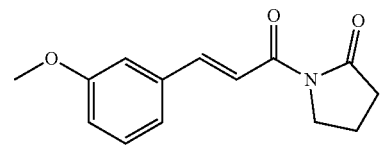 [SMILES: COc1cccc(/C=C/C(=O)N2CCCC2=O)c1] | 245.1052 | $C_{14}H_{15}NO_3$ | 954.5 | 962.8 | 8.3 |
| SHJ-27 | 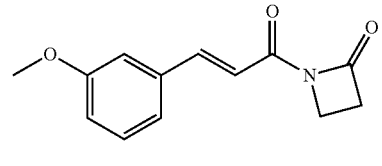 [SMILES: COc1cccc(/C=C/C(=O)N2CCC2=O)c1] | 231.0895 | $C_{13}H_{13}NO_3$ | 950.4 | 955.3 | 4.9 |
| SHJ-31 | 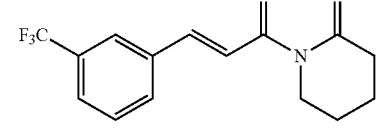 | 297.0977 | $C_{15}H_{14}F_3NO_2$ | 948 | 953.6 | 5.6 |
| SHJ-32 | 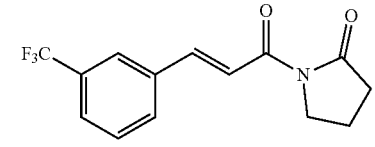 [SMILES: O=C(/C=C/c1cccc(C(F)(F)F)c1)N1CCCC1=O] | 283.082 | $C_{14}H_{12}F_3NO_2$ | 965 | 971.6 | 6.6 |
| SHJ-33 | 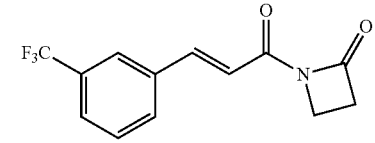 [SMILES: O=C(/C=C/c1cccc(C(F)(F)F)c1)N1CCC1=O] | 269.0664 | $C_{13}H_{10}F_3NO_2$ | 950.8 | 958.1 | 7.3 |

TABLE 1-continued

| Compound ID | Structure | m/z | Mol For | IW | FW | NET Wt (mg) |
|---|---|---|---|---|---|---|
| SHJ-34 | 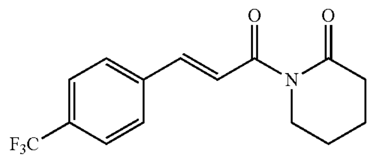 [SMILES: O=C(/C=C/c1ccc(C(F)(F)F)cc1)N1CCCCC1=O] | 297.0977 | $C_{15}H_{14}F_3NO_2$ | 950.8 | 955.6 | 4.8 |
| SHJ-35 | 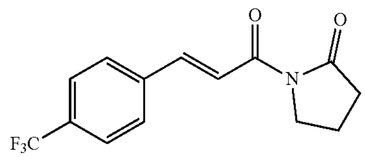 [SMILES: O=C(/C=C/c1ccc(C(F)(F)F)cc1)N1CCCC1=O] | 283.082 | $C_{14}H_{12}F_3NO_2$ | 982.8 | 989.3 | 6.5 |
| SHJ-36 | 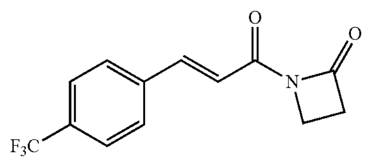 [SMILES: O=C(/C=C/c1ccc(C(F)(F)F)cc1)N1CCC1=O] | 269.0664 | $C_{13}H_{10}F_3NO_2$ | 970.7 | 979.4 | 8.7 |
| SHJ-38 | 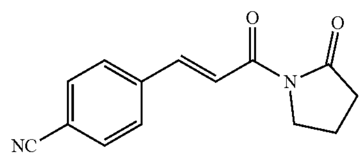 [SMILES: N#Cc1ccc(/C=C/C(=O)N2CCCC2=O)cc1] | 240.0899 | $C_{14}H_{12}N_2O_2$ | 970.7 | 975.7 | 5 |
| SHJ-39 | 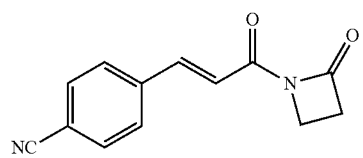 [SMILES: N#Cc1ccc(/C=C/C(=O)N2CCC2=O)cc1] | 226.0742 | $C_{13}H_{10}N_2O_2$ | 948 | 951.8 | 3.8 |
| SHJ-40 | 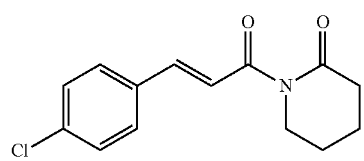 [SMILES: O=C(/C=C/c1ccc(Cl)cc1)N1CCCCC1=O] | 263.0713 | $C_{14}H_{14}ClNO_2$ | 991.5 | 998.8 | 7.3 |
| SHJ-41 | 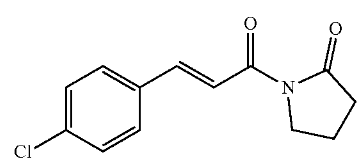 [SMILES: O=C(/C=C/c1ccc(Cl)cc1)N1CCCC1=O] | 249.0557 | $C_{13}H_{12}ClNO_2$ | 968.1 | 975.5 | 7.4 |
| SHJ-42 | 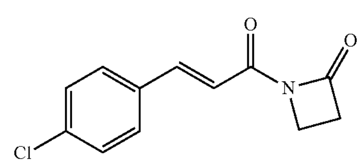 [SMILES: O=C(/C=C/c1ccc(Cl)cc1)N1CCC1=O] | 235.04 | $C_{12}H_{10}ClNO_2$ | 965.2 | 972 | 6.8 |
| SHJ-46 | 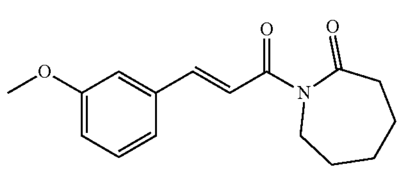 [SMILES: COc1cccc(/C=C/C(=O)N2CCCCCC2=O)c1] | 273.1365 | $C_{16}H_{19}NO_3$ | 942.6 | 955.1 | 12.5 |

TABLE 1-continued

| Compound ID | Structure | m/z | Mol For | IW | FW | NET Wt (mg) |
|---|---|---|---|---|---|---|
| SHJ-48 | 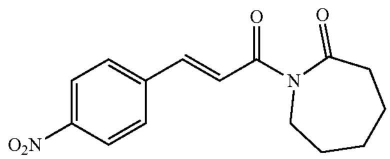 [SMILES: O=C(/C=C/c1ccc([N+](=O)[O-])cc1)N1CCCCCC1=O] | 288.111 | $C_{15}H_{16}N_2O_4$ | 949.8 | 953.8 | 4 |
| SHJ-49 | 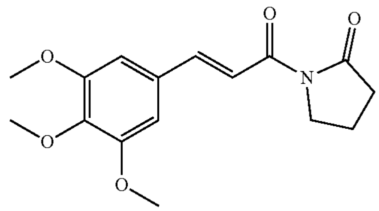 [SMILES: COc1cc(/C=C/C(=O)N2CCCC2=O)cc(OC)c1OC] | 305.1263 | $C_{16}H_{19}NO_5$ | 944.7 | 949.7 | 5 |
| SHJ-50 | 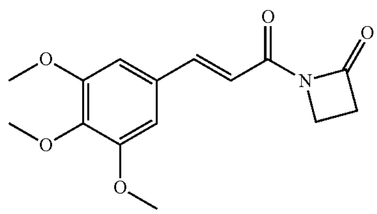 [SMILES: COc1cc(/C=C/C(=O)N2CCC2=O)cc(OC)c1OC] | 291.1107 | $C_{15}H_{17}NO_5$ | 993.9 | 1000.4 | 6.5 |
| SHJ-51 | 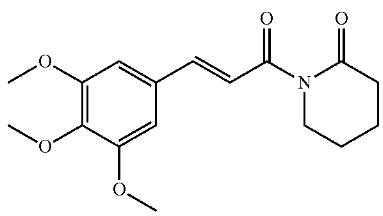 [SMILES: COc1cc(/C=C/C(=O)N2CCCCC2=O)cc(OC)c1OC] | 319.142 | $C_{17}H_{21}NO_5$ | 942.6 | 949.8 | 7.2 |
| SHJ-52 | 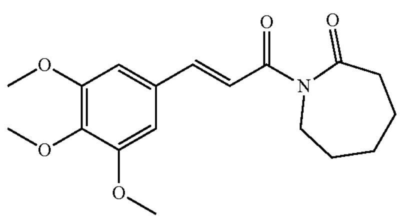 [SMILES: COc1cc(/C=C/C(=O)N2CCCCCC2=O)cc(OC)c1OC] | 333.1576 | $C_{18}H_{23}NO_5$ | 973.6 | 986 | 12.4 |
| SHJ-53 | 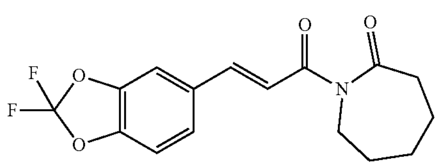 [SMILES: O=C(/C=C/c1ccc2c(c1)OC(F)(F)O2)N1CCCCCC1=O] | 323.0969 | $C_{16}H_{15}F_2NO_4$ | 948.2 | 957.1 | 8.9 |
| SHJ-54 | 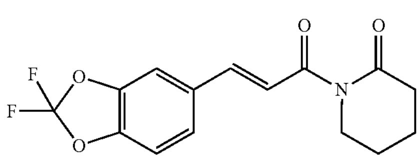 [SMILES: O=C(/C=C/c1ccc2c(c1)OC(F)(F)O2)N1CCCCC1=O] | 309.0813 | $C_{15}H_{13}F_2NO_4$ | 985.8 | 995.6 | 9.8 |
| SHJ-55 | 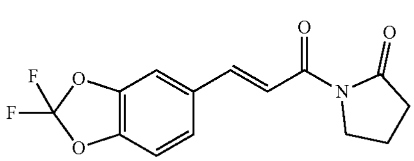 [SMILES: O=C(/C=C/c1ccc2c(c1)OC(F)(F)O2)N1CCCC1=O] | 295.0656 | $C_{14}H_{11}F_2NO_4$ | 960.2 | 966 | 5.8 |

TABLE 1-continued

| Compound ID | Structure | m/z | Mol For | IW | FW | NET Wt (mg) |
|---|---|---|---|---|---|---|
| SHJ-56 | 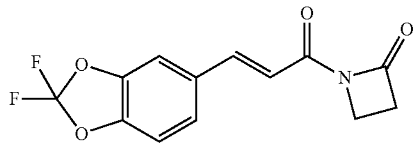 [SMILES: O=C(/C=C/c1ccc2c(c1)OC(F)(F)O2)N1CCC1=O] | 281.05 | $C_{13}H_9F_2NO_4$ | 950.8 | 959.8 | 9 |
| SHJ-57 | 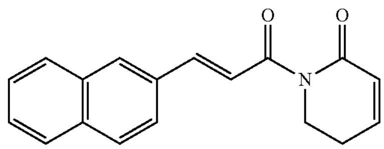 [SMILES: O=C1C=CCCN1C(=O)/C=C/c1ccc2ccccc2c1] | 277.1103 | $C_{18}H_{15}NO_2$ | 943.9 | 948.9 | 5 |

Figure 3:
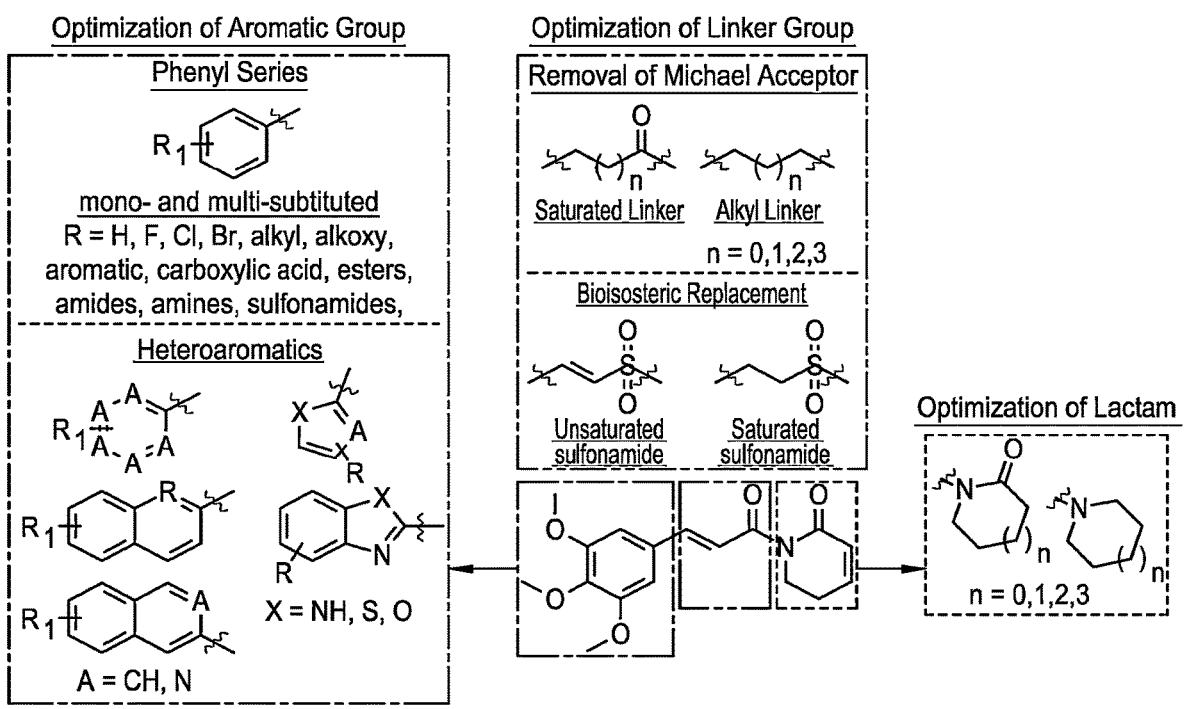
FIG. 3 illustrates a synthetic scheme to make the derivatives of this invention.

The Piperlongumine derivatives of Table 1 may be synthesized by the compounds and formulas described in FIGS. 2-4A&B. Piperlongumine derivatives are derived from the following scheme of reactions:

Now referring to FIG. 3, semi-synthetic optimization of natural products is a methodology that has led to FDA-approved drugs with significant clinical activity. To optimize PG therapeutic potential, we propose the following medicinal chemistry plan to further improve PG otoprotection and biopharmaceutical properties.

The analogs synthesized have focused on para-substituted aromatics to expand SAR on the aromatic ring, we propose two major aromatic series, i) mono- and multi-substituted phenyl rings and ii) unsubstituted and substituted heteroaromatics.

Figure 2:
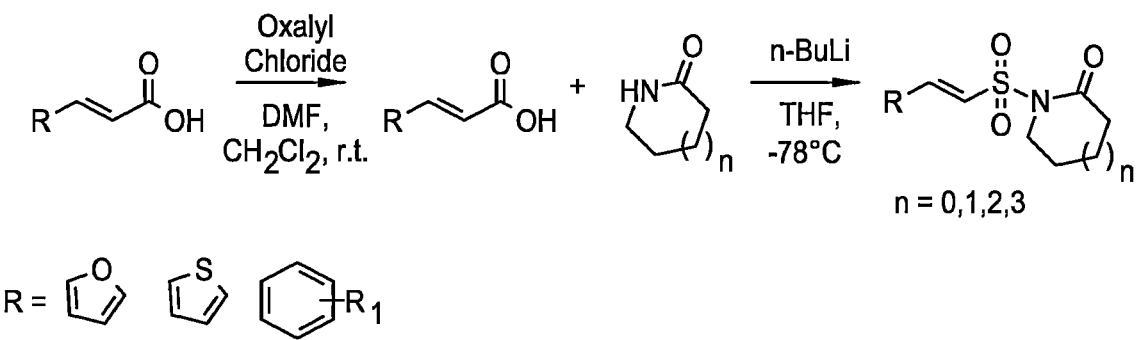
FIG. 2 illustrates a synthetic scheme to make the derivatives of this invention.

In Scheme 1, briefly, commercially available 3-aryl-α,β-unsaturated carboxylic acids were converted to acid chlorides with oxalyl chloride. Various lactams were activated with n-butyl lithium and were reacted with acid. 3-aryl-α,β-unsaturated carboxylic acids were converted to acid chlorides with oxalyl chloride. Various lactams were activated with n-butyl lithium and were reacted with acid chlorides to yield final products. R1=3-methoxy, 3-trifluromethyl, 4-trifluromethyl 4-cyano, 4-nitro, 4-chloro, 3,4,5-trimethoxy 2,2-difluoroacetal(FIG. 2).

In order to synthesize the Piperlongumine derivatives with optimized aromatic groups i) mono- and multi-substituted phenyl rings, and ii) unsubstituted and substituted heteroaromatics scheme 2 (FIG. 2) is followed:

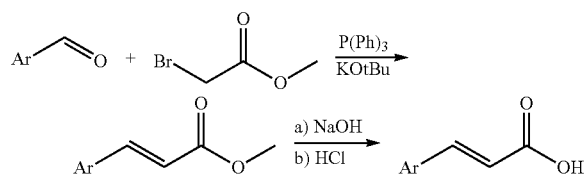

Scheme 2. Synthesis of β-aryl-α,β-unsaturated carboxylic acids the β-aryl-α,β-unsaturated carboxylic acids synthesized are followed by reactions of Scheme 1(FIG. 2).

In scheme 2, β-aryl-α,β-unsaturated carboxylic acids will be synthesized according to Scheme 2. Briefly, aryl or heteroaryl aldehydes will be reacted with methyl 2-bromo acetate under Wittig conditions. Soaponification of the methyl ester will yield β-aryl-α,β-unsaturated carboxylic acids. We plan to synthesize PG analogs with at least 50-75 unique aromatic groups.

Figure 4A:
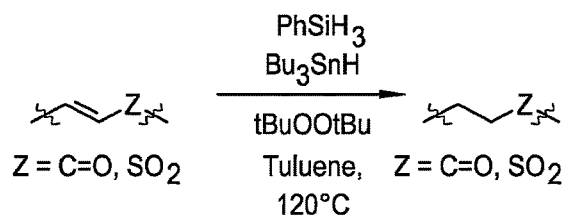
FIGS. 4A and B illustrates synthetic schemes to make the derivatives of this invention.
Figure 4B:
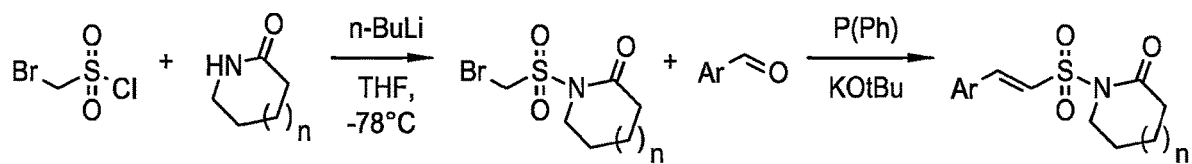

In order to synthesize the Piperlongumine derivatives with optimized linker groups i) saturated amide linker, ii) reduced alkyl linker, iii) β-aryl-α,β-unsaturated sulfonamides, and iv) saturated sulfonamides scheme 3 (FIG. 4A) and 4 (FIG. 4B) are followed:

Saturated amide linker and alkyl linker groups result after Piperlongumine (E)-1-(3-(3,4,5-trimethoxyphenyl)acryloyl)-S,6-dihydropyridin-2(1H)-one analogs are synthesized according to Scheme 1 (FIG. 2) and reduced according to Scheme 3. β-aryl-α,β-unsaturated sulfonamides will be synthesized according to Scheme 4 (FIG. 4B). In scheme 4, 2-bromomethyl sulfonylchloride may be reacted with various lactams in the presence of n-butyl lithium, yielding the sulfonamide.

Compounds are revealed to protect against hair cell apoptosis. Compounds are identified as acting against hair cell loss in animals by the models and data presented. Models reveal properties necessary for an otoprotective compound such as high efficacy against hair cell loss, relatively low toxicity. Compounds are revealed to have high efficacy and high affinity in mouse and zebrafish models used to demonstrate protection against hair cell loss. The lateral-line neuromasts of zebrafish are a valuable model for testing compounds protective against hearing loss in vivo, as their HCs are considered homologous to those in the mammalian inner ear and are readily accessible to drugs in vivo. Teitz et al., J. Exp. Med. 2; 215(4): 1187-1203 (2018). Mouse models involving embryonic fibroblast cell viability have shown effective in validating therapeutic uses of compounds against hearing loss due to cancer treatment such as cisplatin, noise, antibiotics, and aging. Teitz et al., J. Exp. Med. 2; 215(4): 1187-1203 (2018).

The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration. Compounds can be synthesized by a variety of methods known in the art.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, PA 1990.

In various aspects, the disclosed pharmaceutical compositions include the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds. The pharmaceutical carrier employed can be, for example, a solid, liquid, or gas.

The pharmaceutical compositions of the present invention include the compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability.

In various aspects, the compounds of this invention can be used in combination with one or more other drugs, in the form of a kit, to prevention, control, amelioration, or reduction of risk of hearing impairments, when the other drugs can have been known to impair hearing such as an antibiotic. Certain antibiotics, especially aminoglycosides (such as gentamicin, streptomycin, and neomycin). Hearing-related side effects from these antibiotics are most common in people who have kidney disease or who already have ear or hearing problems.

Figure 5A:
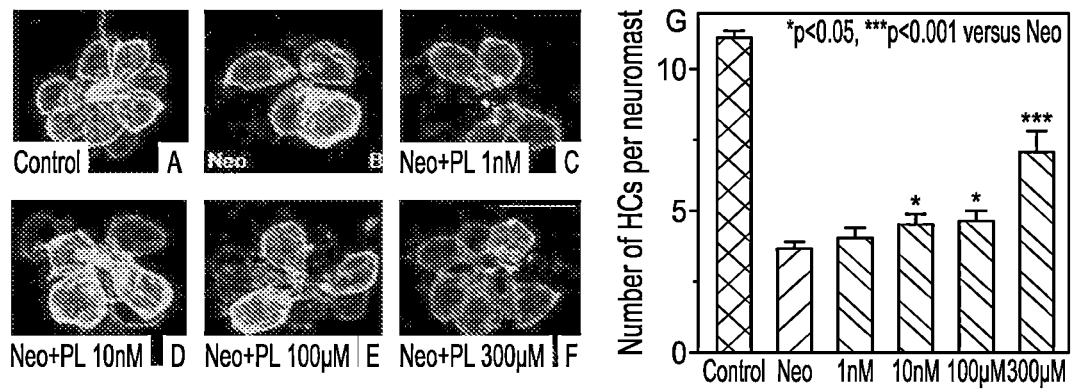
FIGS. 5A-C shows A and B Piperlongumine protects zebrafish neuromasts from neomycin-induced hair cell death and C Piperlongumine protects zebrafish neuromasts from gentamycin-induced hair cell death.
Figure 5B:
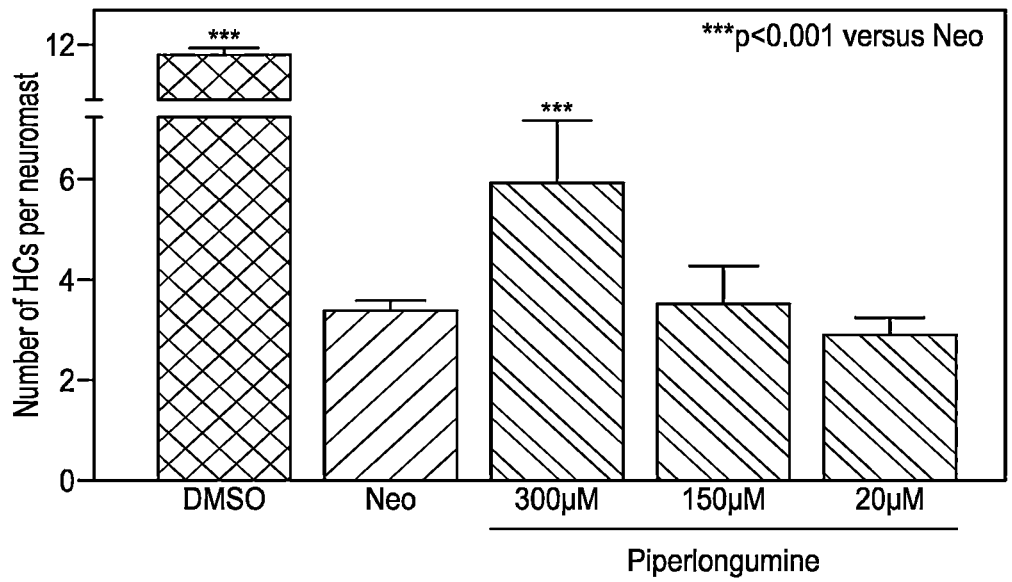
Figure 5C:
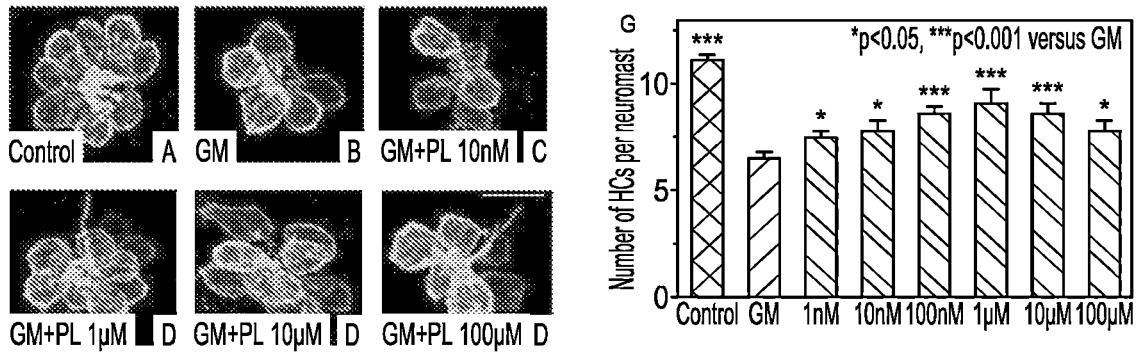

Now referring to FIGS. 5A-C,(E)-1-(3-(3,4,5-trimethoxyphenyl)acryloyl)-5,6-dihydropyridin-2(1H)-one (Piperlongumine) protects from aminoglycoside induced hair cell loss in zebrafish lateral line neuromasts in vivo. Zebrafish lateral line neuromast HC counts are commonly used in vivo models for screening otoprotectants. *Danio rerio* experimental larvae were obtained by pair mating of adult fish maintained at Creighton University by standard methods approved by the Institutional Animal Care and Use Committee. Fish used were Tg(pou4f3:mGFP) expressing a membrane bound GFP in HCs. Experimental fish were maintained at 28.5° C. in E3 media (5 mM NaCl, 0.17 mM KCl, 0.33 mM CaCl2 and 0.33 nM MgSO4, pH 7.2). Animals were cryoanaesthetized after drug treatment and prior to fixation. The neuromasts inspected, SO3 and O1-2, were part of the cranial system and included the otic, middle, and opercular neuromasts. The lateral-line neuromasts of zebrafish are a valuable system for testing protectivity of compounds against aminoglycoside toxicity in vivo, as their HCs are considered homologous to those in the mammalian inner ear and are readily accessible to drugs.

For the screenings, 5-day post-fertilization (dpf) Tg(brn3c:GFP) larvae were pre-incubated with (E)-1-(3-(3, 4,5-trimethoxyphenyl)acryloyl)-5,6-dihydropyridin-2(1H)-one at 10 nM, 10 nM, 1 µM, 10 µM, 100 µM and 300 µM for 1 hour followed by co-incubation with either 200 µM Neomycin (Neo) for 30 minutes (as shown in FIGS. 5A and B), or 100 µM gentamycin (GM) for 1 hour (as shown in FIG. 5C). DMSO, Neo alone, and GM alone were used as a controls for their respective experiments (FIGS. 5A and C).

Figure 6:
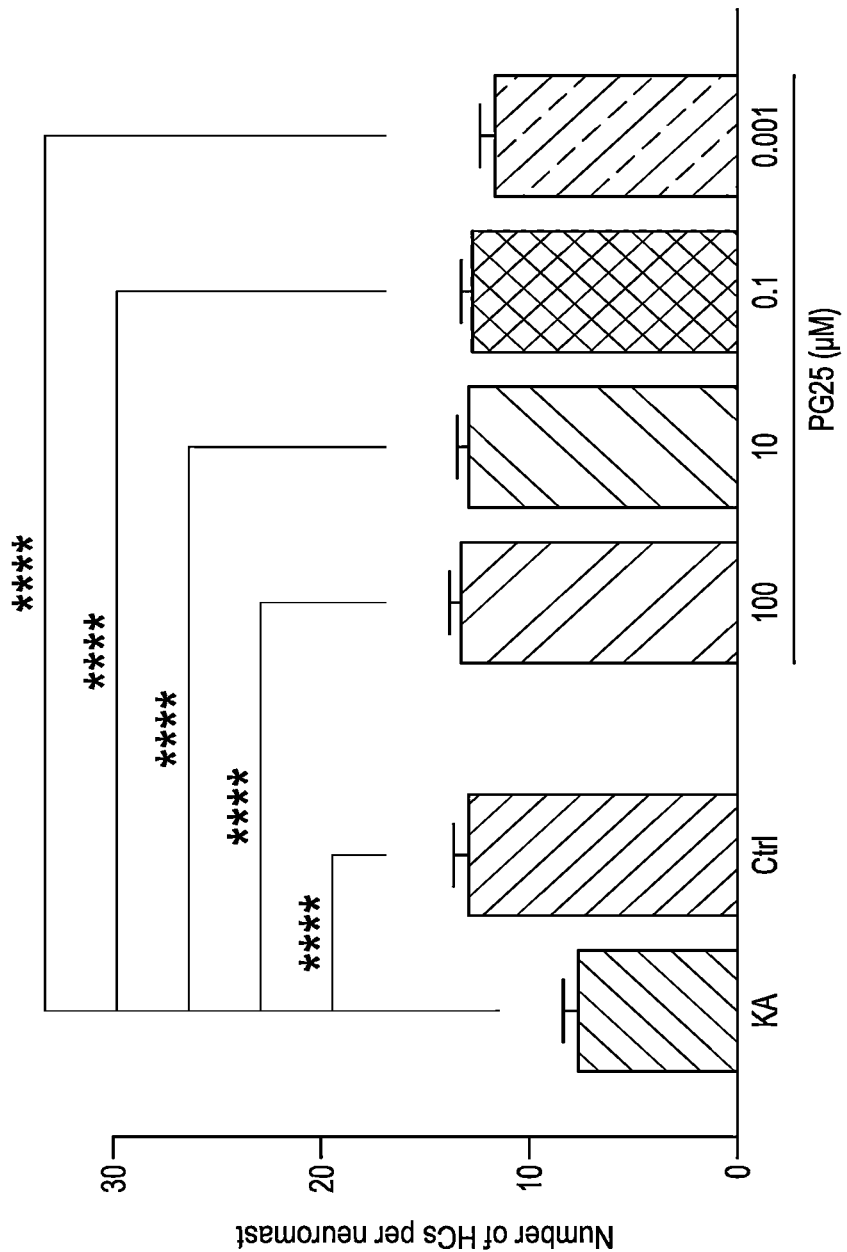
FIG. 6 shows Piperlongumine derivatives protect zebrafish neuromasts from excitotoxic damage. 5dpf Tg(Brn3c:mGFP) larvae were used for the experiments. Zebrafish were pretreated with kainic acid for one hour (300 µM) to mimic the excitotoxic damage induced by noise exposure, and then, post-treated with Piperlongumine-25 for 2 hours (al concentrations of 0.001 µM; 0.1 µM; 10 µM; and 100 µM). Control animal were treated with DMSO (−) or Piperlongumine-25 alone (+). Animals were then fixed and immunostained for GFP. Quantification was done by assessing three neuromasts in the same anatomic location of each animal (n=5). The data is plotted as mean+SD. Statistical testing was done with One-way ANOVA and Dunnett post-hoc test ($P<0.0001$ compared to KA).

Subsequently, animals were transferred to E3 water for 5 hours and fixed in 4% paraformaldehyde (PFA) overnight. Neuromast HCs were immunolabeled with anti-otoferlin (HCS-1, DSHB) and anti-GFP (NB100-1614, Novus Biologicals). These two markers were used to detect and count neuromast HCs to reduce the chances of missing some of the HCs after the treatment since as it was previously noticed that incubation with the compounds can affect GFP expression more difficult to detect under a fluorescence microscope. Otic, middle, and opercular neuromasts were identified, and HCs at SO3 (supraorbital line neuromast) and O1-2 (Otic line neuromasts) were manually counted using a Zeiss AxioSkop 2 fluorescence microscope with a 40× oil objective. Control animals were treated with DMSO (−) or Neo or GM alone (+) Animals were then fixed and immunostained for GFP and otoferlin. Quantification was done by assessing three neuromasts in the same anatomic location of each animal (n=5). The data is plotted as mean+SD. Statistical testing was done with One-way ANOVA and Dunnett post-hoc test (*$P<0.05$, $P<0.01$, *$P<0.001$ compared to either Neo or GM, respectively). Now referring to FIG. 6 Piperlongumine-25 protects neuromast hair cells from excitotoxic damage induced by kainic acid (KA). For the screening of piperlongumine derivatives for protection against noise-induced hearing loss we employed a zebrafish model that mimics excitotoxic damage. Five-day post-fertilization (dpf) Tg(brn3c:GFP) larvae were incubated with 300 µM of KA for 1 hour followed by piperlongumine-25 for 2 hours at 0.001 µM, 0.1 µM, 10 µM, and 100 µM. DMSO and KA were used as controls. Additionally, 5-day post-fertilization (dpf) Tg(brn3c:GFP) larvae were incubated with Piperlongumine-25 alone for 2 hours to confirm that by itself does not result in any general toxicity.

Figure 7:
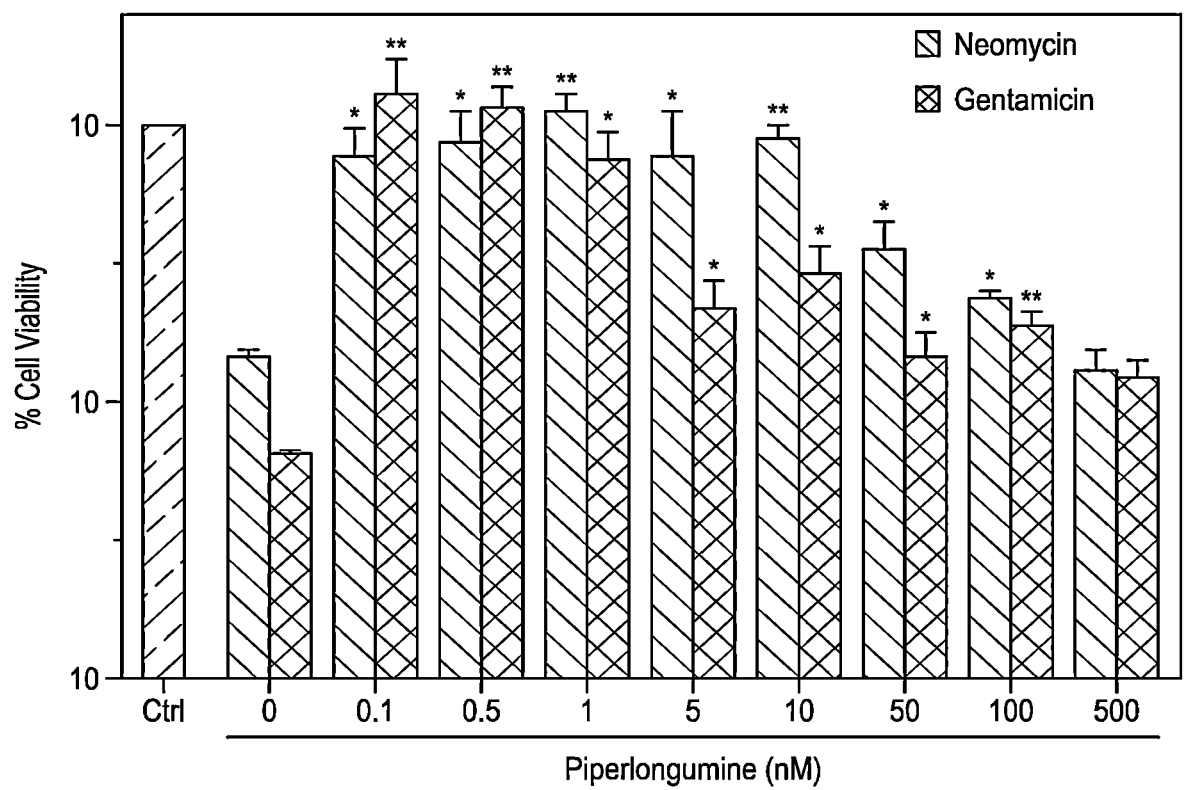
FIG. 7 shows protection of mouse embryonic fibroblast (MEFs) by Piperlongumine against aminoglycosides. MEFs were incubated for 15 hours with neomycin (100 µM) or gentamicin (8 µM) with or without Piperlongumine (0.1 nM-5 µM). Cell viability was assessed employing MTT (3-(4-,5-dimethylthiazol-2-yl)-2,5-diphenyltetrazolium bromide) viability kit test (Thermo Fisher). The data is plotted as mean+SD. Statistical testing was done with One-way ANOVA and Dunnett post-hoc test (*P<0.05, **P<0.01 compared to either Neo or GM, respectively).

Now referring to FIG. 7 (E)-1-(3-(3,4,5-trimethoxyphenyl)acryloyl)-S,6-dihydropyridin-2(1H)-one protects mouse embryonic fibroblast (MEFs) against aminoglycosides. MEFs were incubated for 15 hours with neomycin (100 µM) or gentamicin (8 µM) with or without(E)-1-(3-(3,4,5-trimethoxyphenyl)acryloyl)-S,6-dihydropyridin-2(1H)-one (0.1 nM-5 µM) at 0.1 nM, 0.5 nM, 1 nM, 5 nM, 10 nM, 50 nM, 100 nM, and 500 nM. Cell viability was assessed employing MTT (3-(4-,5-dimethylthiazol-2-yl)-2,5-diphenyltetrazolium bromide) viability kit test (Thermo Fisher). The data is plotted as mean+SD. Statistical testing was done with One-way ANOVA and Dunnett post-hoc test (*P<0.05, **P<0.01 compared to either Neo or GM, respectively). 100% protection by (E)-1-(3-(3,4,5-trimethoxyphenyl)acryloyl)-S,6-dihydropyridin-2(1H)-one was observed at 0.1 nM to 10 nM against neomycin and 0.1 nM to 1 nM against gentamycin.

Figure 8A:
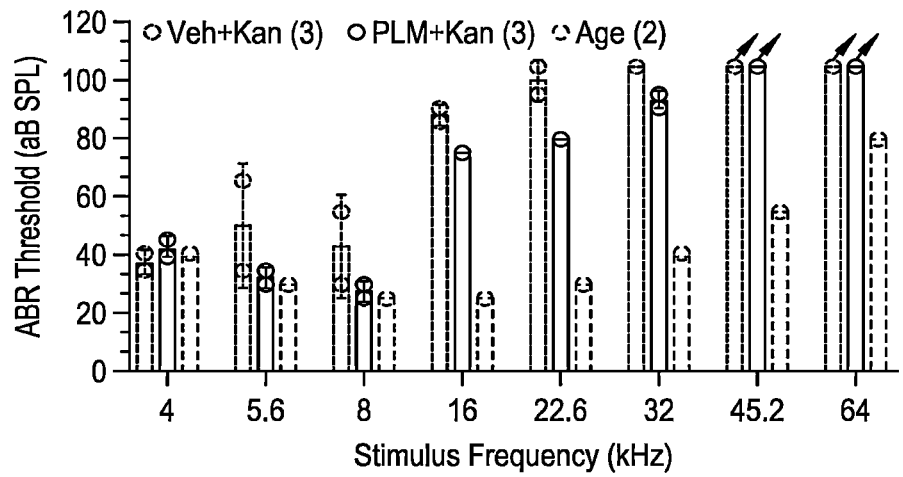
FIGS. 8A and B shows A(E)-1-(3-(3,4,5-trimethoxyphenyl)acryloyl)-S,6-dihydropyridin-2(1H)-one preserves normal hair cell function in antibiotic exposed mice. C57BI6 (Cdh23 corrected) (6-7 weeks old) were exposed to vehicle+ kanamycin (Veh+Kan) (700 mg/kg b.w. twice a day for 14 days) (shown as circles with four breaks); or (E)-1-(3-(3,4,5-trimethoxyphenyl)acryloyl)-S,6-dihydropyridin-2(1H)-one+kanamycin (PLM+Kan) with (E)-1-(3-(3,4,5-trimethoxyphenyl)acryloyl)-S,6-dihydropyridin-2(1H)-one (40 mg/kg b.w. once a day for 17 days) (shown as circle no breaks). Age match controls are shown (age, shown as circle with three breaks). Auditory brainstem response (ABR) thresholds were recorded for frequencies (4 kHz, 5.6 kHz, 8 kHz, 16 kHz, 22.6 kHz, 32 kHz, 45.2 kHz, and 64 kHz) before and after treatment protocol. We observed significant protection when animals were co-treated with PLM at 22.6 KHZ compared to animals Kan alone. Statistical analysis was done with repeated measures ANOVA between groups. B shows Piperlongumine(E)-1-(3-(3,4,5-trimethoxyphenyl)acryloyl)-S,6-dihydropyridin-2(1H)-one is not toxic with and without kanamycin exposure in C57BI6 mice in vivo over the 17-day treatment regimen.

Now referring to FIG. 8A, Piperlongumine protects from aminoglycoside toxicity in mice in vivo. 6-7-week-old C57BL/6 (Cdh23 corrected) were used, with a mix of males and females across experiments. Procedures were approved by the IACUC committee of the Creighton University.) Mice were treated with Piperlongumine (40 mg/kg b.w., for 17 days, IP) with or without kanamycin treatment (700 mg/kg b.w. for 14 days twice a day, s.q.). Piperlongumine's protection against hearing impairment loss was assessed by measuring ABR threshold shifts in the mouse ear.

Animals were anesthetized with a mixture of ketamine/xylazine before ABR assessment. Subcutaneous needle electrodes were inserted behind the pinna (inverting), vertex of the skull (non-inverting) and base of the tail (ground). Tone bursts of 5 ms duration with 0.5 ms cosine-squared envelopes delivered at a rate of 21 stimuli per second with alternating polarity were generated using BioSigRZ software and RZ6 multi I/O processor system (Tucker-Davis Technologies, FL). Stimuli were presented as open field via a speaker (MF1; TDT, FL) placed 10 cm in front of the pinna of the animal. Evoked responses were amplified (20x), bandpass filtered (300-3,000 Hz) and average of 512 responses of 10 ms duration was recorded. Stimulus intensity was decreased in 5 dB increments, starting from 100 db SPL to 0 dB SPL. Thresholds at 4, 5.6, 8,16, 22.6, 32, 45.2, and 64 kHz were identified by visual inspection from stacked waveforms as the lowest level at which reproducible response could be identified. Before the start of every session, stimulus presenting speaker (MF1) was calibrated with a ¼" microphone (PCB-378C10; PCB Piezotronics, NY) that was also placed 10 cm in front of the speaker. Similar experiments have been previously described in Rai V. et al., Sci Rep. 2020 Sep. 16; 10(1):15167.

Age-control group mice were administered saline. Significant differences in threshold were observed at 22.6 kHz (p=0.0408, 2-way ANOVA with Holm Sidak's multiple comparison). Data are presented as mean+SD, n=3-4/group.

Figure 8B:
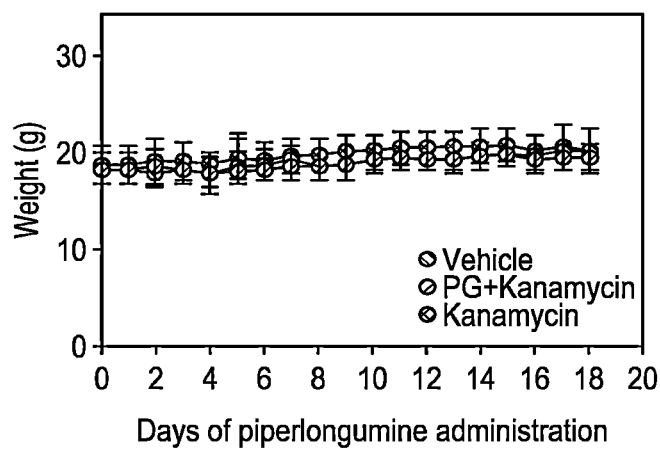

Now referring to FIG. 8B, kanamycin alone and in combination with (E)-1-(3-(3,4,5-trimethoxyphenyl)acryloyl)-S,6-dihydropyridin-2(1H)-one showed no general toxicity in C57BL/6 mice (Cdh23 corrected) during the 17-day exposure period.

Figure 9A:
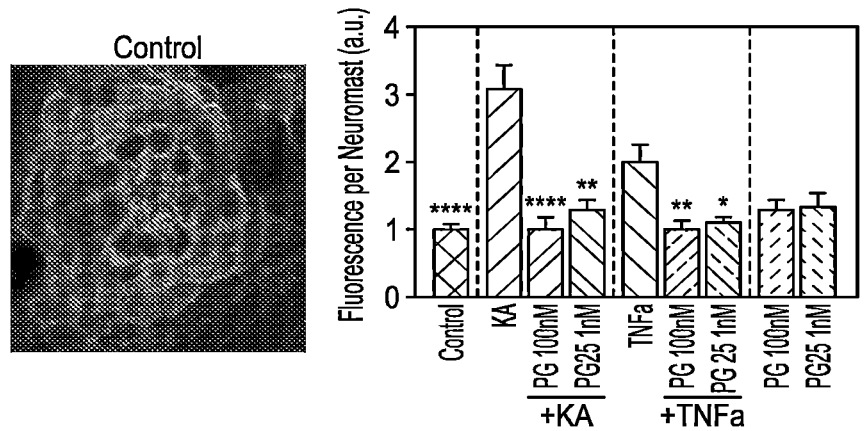
FIG. 9 shows Piperlongumine (E)-1-(3-(3,4,5-trimethoxyphenyl)acryloyl)-S,6-dihydropyridin-2(1H)-one and its derivatives reduce NF-kB activity in zebrafish.
Figure 9B:
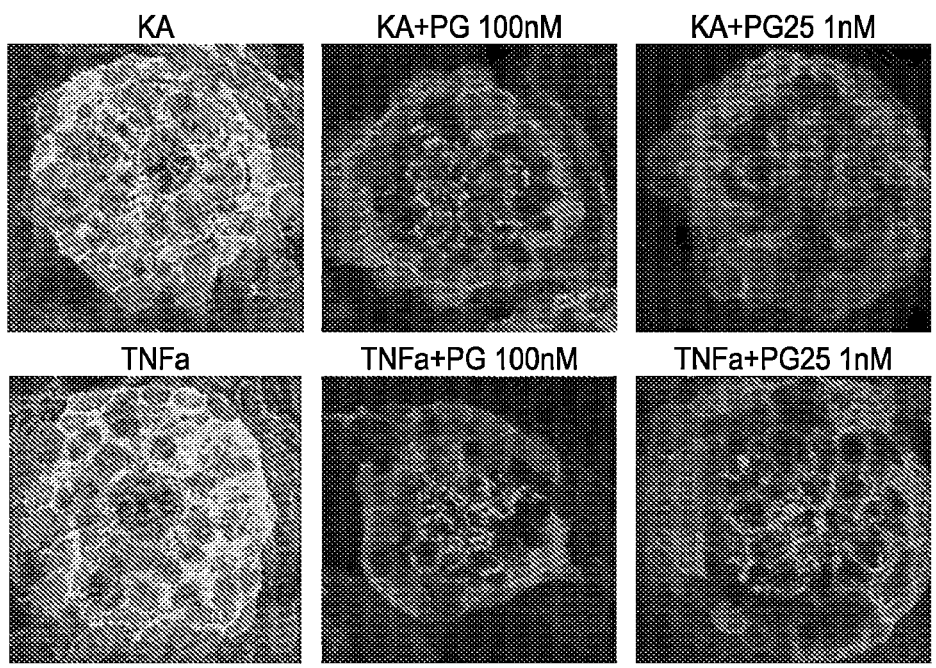

Now referring to FIG. 9, to confirm that(E)-1-(3-(3,4,5-trimethoxyphenyl)acryloyl)-S,6-dihydropyridin-2(1H)-one and its derivates work by inhibiting NF-kB activity a set of experiments were performed. Zebrafish reporter line that expresses GFP under the NF-kB promoter were used. In individual experiments, at 5dpf animals were incubated with vehicle (E3 water), KA 300 µM for 1 hour or 10 ng/mL TNFa for 30 minutes to induce the NF-kB pathway. Next, zebrafish were incubated with vehicle (DMSO 0.1%), or with (E)-1-(3-(3,4,5-trimethoxyphenyl)acryloyl)-S,6-dihydropyridin-2(1H)-one or one of its derivatives at 1 nM and 100 nM for 2 hours. Zebrafish neuromast were fixed and immunostained for GFP (green) and otoferlin (red). The fluorescence intensity of GFP (used as a proxy for NF-kB activation) was quantified employing ImageJ and expressed as arbitrary florescence units per neuromast. TNFa, an activator of NF-kB, was used a positive control. Zebrafish incubated with(E)-1-(3-(3,4,5-trimethoxyphenyl)acryloyl)-S,6-dihydropyridin-2(1H)-one at 100 nM or Piperlongumine-25 (PG25 ((SHJ-25)) at 1 nM showed a reduction of NF-kB pathway activation compared to fish exposed to KA or TNFa alone. Piperlongumine (E)-1-(3-(3,4,5-trimethoxyphenyl)acryloyl)-S,6-dihydropyridin-2(1H)-one at 100 nM or Piperlongumine-25 PG25 ((SHJ-25)) at 1 nM showed a reduction of NF-kB pathway activation compared to fish exposed to KA or TNFa alone.

Zebrafish were incubated with vehicle (control), KA 300 µM (KA), or TNFa (10 ng/mL) (TNFa) alone or in combination with Piperlongumine (E)-1-(3-(3,4,5-trimethoxyphenyl)acryloyl)-S,6-dihydropyridin-2(1H)-one or one of its derivatives for 2 hours at concentrations of 1 nM or 100 nM. Animals were fixed and immunostained for GFP (green) and otoferlin (red). GFP fluorescence intensity was quantified with ImageJ and expressed as mean+/−SEM. Statistical analysis: One-Way ANOVA. (*p,0.05, p<0.01, **p<0.0001, compared to the corresponding ototoxin alone). Piperlongumine (E)-1-(3-(3,4,5-trimethoxyphenyl) acryloyl)-S,6-dihydropyridin-2(1H)-one 100 nM or Piperlongumine-25 (PG25 1 nM showed a reduction of NF-kB pathway activation compared to fish exposed to KA or TNFa alone.

Figure 10:
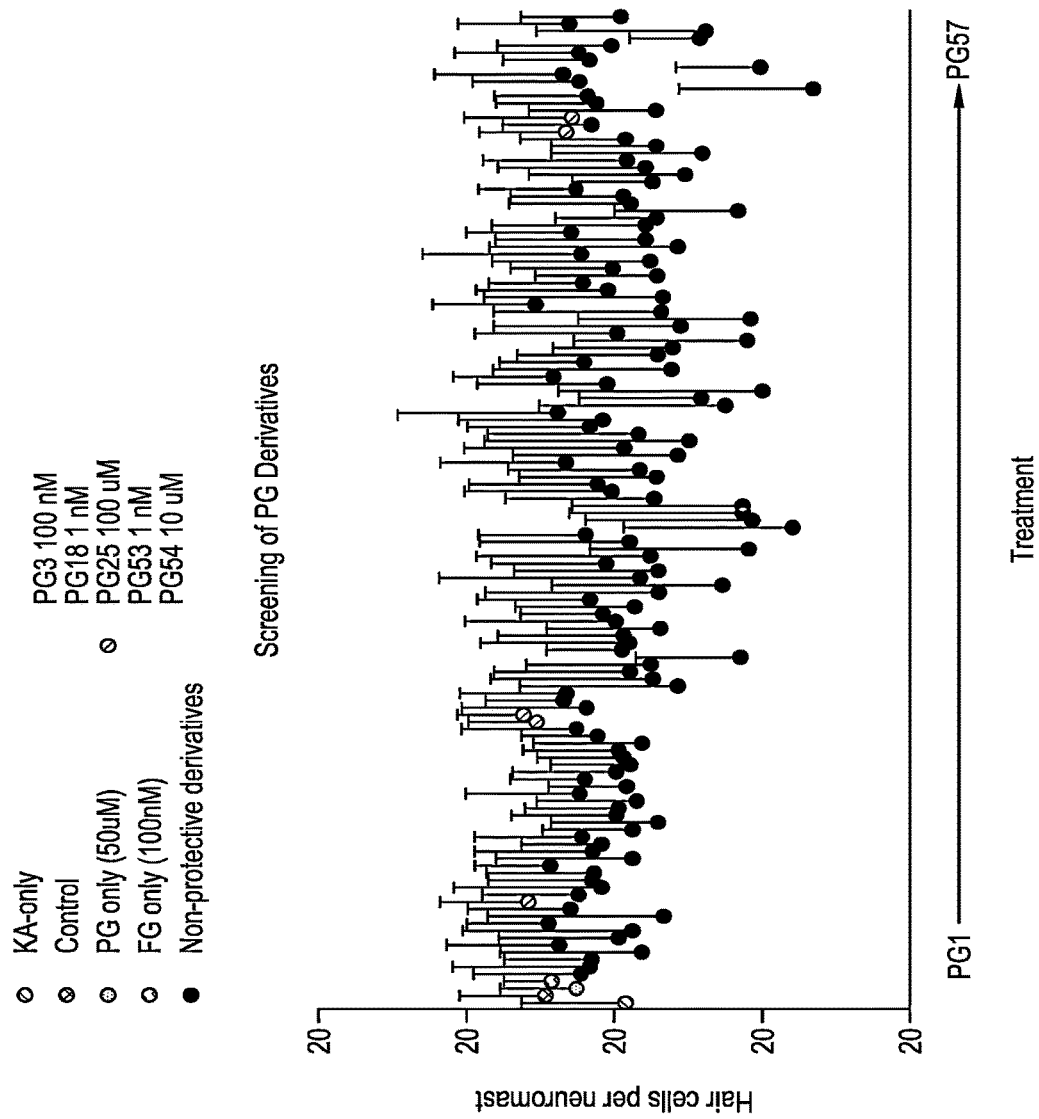
FIG. 10 shows Piperlongumine derivatives were tested in a zebrafish model for excitotoxicity.
Figure 11:
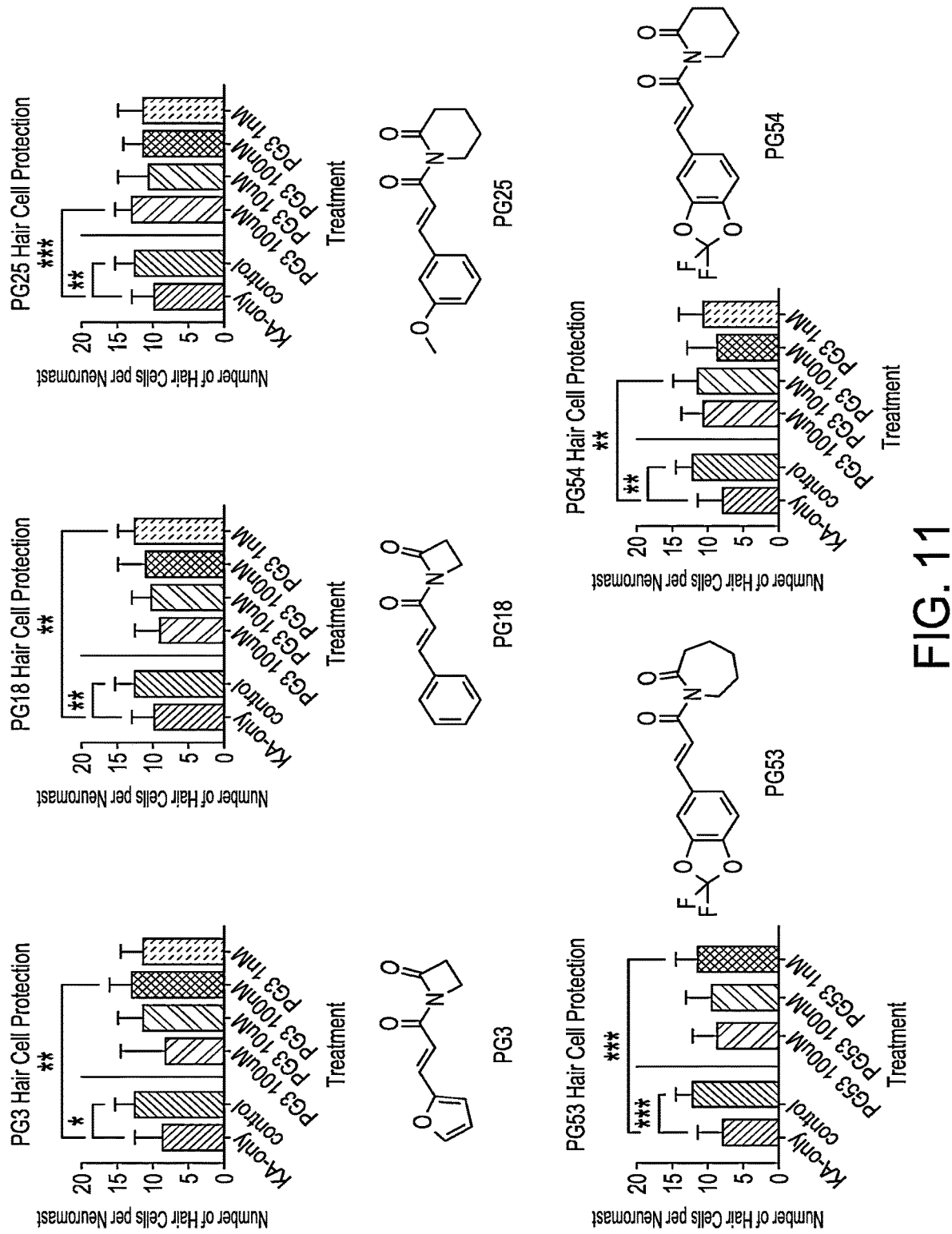
FIG. 11 shows Piperlongumine derivatives PG3, PG18, PG25, PG53 and PG54 performed better than Piperlongumine in a zebrafish model for excitotoxicity.

Now referring to FIGS. 10 and 11 Of the derivates of Piperlongumine tested, PG3 (SHJ-3), PG 18 (SHJ-18), PG25 ((SHJ-25), PG 53 (SHJ-53) and PG 54 (SHJ-54) had better performance than Piperlongumine against kainic acid (KA) induced hair cell death.

FIG. 10 shows Piperlongumine derivatives were tested in a zebrafish model for excitotoxicity. 5 dpf fish were incubated with KA 300 µM for 1 hour followed by a two-hour incubation with one of the piperlongumine derivatives at 1 nM to 100 µM. Animals were fixed and immunostained for the hair cell marker, otoferlin. Neuromast hair cells were counted under a fluorescence microscope. At least 3 neuromast of the rostral lateral line were inspected per fish, in a total of 6 fish per treatment. Results are presented as mean+/−SD. Control, KA only, PG only, PG+KA, derivatives that were no protective against excitotoxicity, derivatives that performed better than PG. (The legend shown in the FIG. 10), FIG. 11 shows PG3, PG18, PG25, PG53 and PG54 performed better than piperlongumine in a zebrafish model for excitotoxicity. 5dpf fish were incubated with KA 300 µM for 1 hour followed by one of the PG derivatives at different concentrations for additional 2 hours. Animals were fixed and immunostained for otoferlin. Neuromast hair cells were quantified in at least 3 rostral neuromasts per fish in a total of 6 fish per treatment. Results are expressed as mean+/−SD. Statistical analysis: One-way ANOVA *P<0.05, **P<0.01, P<0.001 versus KA alone. These five Piperlongumine derivatives performed better than Piperlongumine at least one dose.

All publications, patents and patent applications mentioned in this specification are herein incorporated by reference to the same extent as if each individual publication, patent, or patent application was specifically and individually indicated to be incorporated by reference.

While the invention has been described with reference to details of the illustrated embodiments, these details are not intended to limit the scope of the invention as defined in the appended claims. The embodiment of the invention in which exclusive property or privilege is claimed is defined as follows:

What is claimed:

1. A method to prevent or treat hearing loss caused by excitotoxic damage comprising: administering to an animal or human in need thereof an effective amount of a pharmaceutical composition containing a therapeutically active agent, wherein the therapeutically active agent is a derivative of Piperlongumine, wherein the Piperlongumine derivative is selected from a group consisting of:

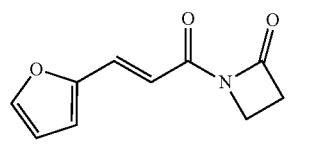

(PG3 (SHJ-3))

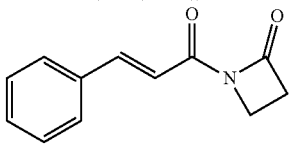

(PG 18(SHJ-18)

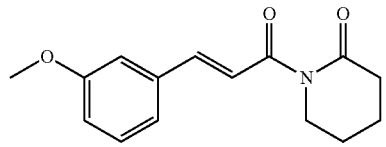

(PG25 ((SHJ-25))

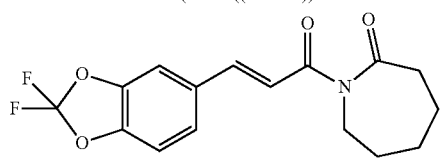

(PG 53 (SHJ-53))   or

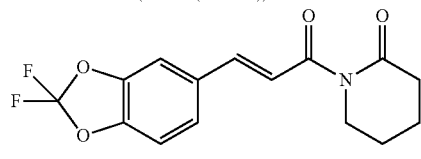

(PG 54 (SHJ-54))

2. The method of claim 1, comprising protecting the inner ear cells from death caused by an antibiotic.

3. The method of claim 1 wherein the antibiotic is an aminoglycoside.

4. The method of claim 1 comprising protecting the inner ear cells from death caused by noise.

5. The method of claim 1 comprising protecting the inner ear cells from death caused by cisplatin treatment.

6. The method of claim 1, wherein the derivative of Piperlongumine (PG3 (SHJ-3)) is comprised of the formula:

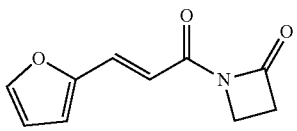 [SMILES: O=C(/C=C/c1ccco1)N1CCC1=O]

7. The method of claim 1, wherein the derivative of Piperlongumine (PG 18 (SHJ-18)) is comprised of the formula:

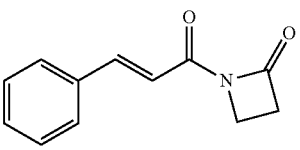 [SMILES: O=C(/C=C/c1ccccc1)N1CCC1=O]

8. The method of claim 1, wherein the derivative of Piperlongumine (PG25 ((SHJ-25)) is comprised of the formula:

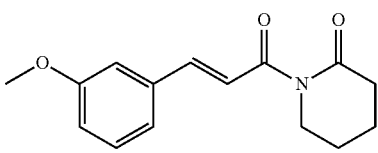 [SMILES: COc1cccc(/C=C/C(=O)N2CCCCC2=O)c1]

9. The method of claim 1, wherein the derivative of Piperlongumine (PG 53 (SHJ-53)) is comprised of the formula (C16H15F2NO4):

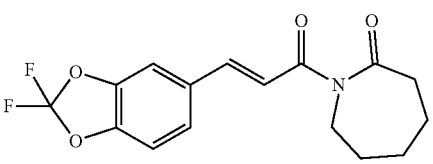 [SMILES: O=C(/C=C/c1ccc2c(c1)OC(F)(F)O2)N1CCCCCC1=O]

10. The method of claim 1, wherein the derivative of Piperlongumine (PG 54 (SHJ-54)) is comprised of the formula (C15H13F2NO4):

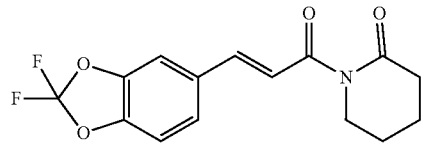 [SMILES: O=C(/C=C/c1ccc2c(c1)OC(F)(F)O2)N1CCCCC1=O]

11. The method of claim 2, comprising protecting the inner ear cells from death caused by neomycin.

12. The method of claim 2, comprising protecting the inner ear cells from death caused by kanamycin.

* * * * *